(12) United States Patent
Bush et al.

(10) Patent No.: US 8,753,609 B2
(45) Date of Patent: Jun. 17, 2014

(54) FLUID BED MEAL CONTAINING A MARKER AND METHODS OF MAKING

(75) Inventors: Kerry C. Bush, Brentwood, TN (US); Stanley J. Konopka, Franklin, TN (US); Ronald W. Sanda, Nashville, TN (US)

(73) Assignee: Advanced Breathe Diagnostics, LLC, Brentwood, TN (US)

( * ) Notice: Subject to any disclaimer, the term of this patent is extended or adjusted under 35 U.S.C. 154(b) by 489 days.

(21) Appl. No.: 12/997,139

(22) PCT Filed: Jun. 10, 2009

(86) PCT No.: PCT/US2009/046867
§ 371 (c)(1),
(2), (4) Date: Jun. 1, 2011

(87) PCT Pub. No.: WO2009/152222
PCT Pub. Date: Dec. 17, 2009

(65) Prior Publication Data
US 2011/0223104 A1 Sep. 15, 2011

Related U.S. Application Data

(60) Provisional application No. 61/060,170, filed on Jun. 10, 2008.

(51) Int. Cl.
*A61K 49/00* (2006.01)
*A61K 51/00* (2006.01)
*A61K 35/54* (2006.01)
*A61K 9/00* (2006.01)

(52) U.S. Cl.
USPC ........ 424/9.2; 424/1.61; 424/195.17; 424/581

(58) Field of Classification Search
None
See application file for complete search history.

(56) References Cited

U.S. PATENT DOCUMENTS

| 5,785,949 | A | 7/1998 | Klein | |
|---|---|---|---|---|
| 6,548,043 | B1 * | 4/2003 | Wagner et al. | 424/1.81 |
| 7,785,569 | B2 * | 8/2010 | Evans et al. | 424/9.2 |
| 2003/0211042 | A1 * | 11/2003 | Evans et al. | 424/9.2 |

FOREIGN PATENT DOCUMENTS

| EP | 1491252 A1 | 12/2004 |
|---|---|---|
| GB | 2360845 | 10/2001 |
| WO | 97/35622 | 10/1997 |
| WO | 03094976 A1 | 11/2003 |

OTHER PUBLICATIONS

C-Breath Tests in Medical Research and Clinical Diagnosis, 4th edition, Printed in May 2005.*
Schuster et al. (2002) Schuster Atlas of Gastrointestinal Motility in Health and Disease, B.C. Decker, $2^{nd}$ Ed., pp. 203-218.*
K. Dewettinck et al., "Fluidized bed coating in food technology" Trends in Food Science & Technology, vol. 10, 1999, pp. 163-168, XP002567303.
Hitomi Yamamoto, "Drying of food and the its related technology," proceeding of 18th spring study regular meeting, MRC37, pp. 42-51, 2007, partial translation.
Kazunori Wakiya et al., Japan Food Science, vol. 41 (6), pp. 41-42, 2002, partial translation.
Hiroyuki Wakya, et al., Chemical Equipment, vol. 39(3), pp. 48-53,1997, partial translation.
Hiroyuki Tsujimoto, Atomiozation, vol. 7(20), pp. 463-472, 1998, partial translation.

* cited by examiner

*Primary Examiner* — Lisa J Hobbs
(74) *Attorney, Agent, or Firm* — Fredrikson & Byron, P.A.

(57) ABSTRACT

A standardized, edible food containing a label for use in the measurement of gastric emptying by the quantification of marker excreted in the breath of the patient and methods of making the same using fluid bed granulation processing.

23 Claims, No Drawings

FLUID BED MEAL CONTAINING A MARKER AND METHODS OF MAKING

CROSS-REFERENCE TO RELATED TO APPLICATIONS

The present application claims priority to International Application No. PCT/US2009/046867 filed Jun. 10, 2009, which in turn claims priority to U.S. Provisional Application No. 61/060,170 filed Jun. 10, 2008, the teachings of which are incorporated Herein by reference.

FIELD OF THE INVENTION

This invention relates generally to a fluid bed standardized meal including an edible food, a component of which includes a marker or drug and methods for using same for reliably delivering a marker or drug into a mammal and the use of that meal for measuring the absorption of therapeutic and diagnostic drugs or markers across an array of highly standardized meals. It also relates to a method of validating a meal to be used in diagnostic or test methods. Furthermore, the meal may be used to measure bodily (physiological) functions as a result of the digestion, absorption and/or metabolism of the meal and its marker or drug.

BACKGROUND OF THE INVENTION

Digestion of consumed foodstuffs begins in the oral cavity where food is mechanically broken down by mastication, lubricated with saliva, and enzymatically processed by amylase present in the saliva. Digestion continues in the stomach where food is liquefied by gastric juices and enzymes secreted by the cells lining the stomach to produce chyme. Chyme enters the small intestine via the pyloric sphincter for further processing by bile salts produced by the liver and pancreatic digestive enzymes. Components not absorbed by or transported into the small intestine are subject to subsequent processing in the large intestine.

The rate at which chyme travels to the small intestine (gastric emptying rate) is the product of numerous physiological factors including, hormones, chemical signals in the ingesta, as well as signals from the nervous system.

A number of the population are affected by disorders that affect the emptying rate. For example, when the rate is accelerated, undigested food is prematurely dumped from the stomach to the small intestine. Conversely, when the rate is decelerated, the movement of ingested food from the stomach to the small intestine is delayed, giving rise to the condition termed "delayed emptying" otherwise known as gastroparesis.

Disorders involving gastric emptying rate are typically diagnosed by monitoring the rate at which a meal empties from the stomach and enters the small intestine. In these tests, typically, an edible food is used to transport a marker into the gut of an animal and gastric emptying monitored by the marker.

Currently, the routine (gold standard) method for quantifying the rate of gastric emptying in humans is quantitative gastric scintigraphy. Scintigraphy involves the ingestion of a meal including at least one edible food, a component of which has been radiolabeled, and the subsequent measurement of gamma emission by a scintillation camera (positioned over the stomach) as the labeled food is emptied from the stomach.

The most common type of meal used in scintigraphy measurement of gastric emptying is a meal typically made by cooking 0.5 mCi $^{99m}Tc$ sulphur colloid with two raw eggs or 120 grams of a liquid egg substitute such as the product sold by ConAgra under the trademark Egg Beater®. In typical use, the patient fasts the night before the test. At the time of the test, the patient consumes the cooked radiolabeled egg component with two slices of bread, 30 grams of jam and 120 ml of water. Scintigraphic scanning with anterior and posterior cameras is performed immediately after the test meal is consumed and scans are obtained every 15 minutes for two hours and every 30 minutes for up to six hours. Scintigraphy measurements of gastric emptying are direct, since the camera directly measures the meal exiting the stomach.

Scintigraphic results may be reported as "Percent Meal Emptied" or inversely, "Percent Meal Retained." Typically, the % meal retained is calculated and reported at the 1, 2, 3, and 4 hour time point based on the amount of gamma radiation appearing at each respective time point. With time, more and more of the meal is emptied and hence there is less and less gamma radiation to be observed from the stomach. An evolving scintigraphic metric in the GI community defines slow gastric emptying as >10% of a meal remaining at the 4-hour time point when utilizing ~225 kcal meal that has been demonstrated to empty in about 4 hours in healthy individuals. The greater the percent retained, the slower the gastric emptying rate. Two additional parameters are clinically useful in scintigraphic scanning. The first, $t_{LAG}$, is the time required for the first 10% of the food to empty from the stomach. The second, $t_{1/2}$, is the time required for half of the contents to be emptied from the stomach. Percent gastric retention of the radiolabel is calculated at each time point to generate a scintigraphic gastric retention curve. The curve is mathematically modeled with a power exponential model and the diagnostic result $t_{LAG}$ and $t_{1/2}$ can be calculated from the curve.

Several disadvantages are associated with the traditional scintigraphy method. First, patients must be subjected to radioisotopes. This is particularly problematic for women of childbearing age or children. Further, the procedure must be carried out at specialized nuclear medicine facilities. Finally, the preparation for the procedure is cumbersome and potentially can introduce error to the test procedure. Prior to the procedure, personnel must prepare the labeled meal. Because cooking parameters or food quality, consistency and meal matrix may vary from hospital to hospital, standardization is lacking. For example, the caloric value, the matrix of meal and amount of scintigraphic scanning time vary from testing center to testing center. As with any medical test, standardization is of significant importance in gastric emptying test procedures.

Recently, a method for measuring the rate of gastric emptying has been described that utilizes an edible food labeled with non-radioactive markers. As the non-radioactive labeled edible food is digested, a labeled component is produced which can be detected in the patient's breath. This method is described in detail in Applicant's U.S. Pat. No. 5,707,602, the teachings of which are hereby incorporated by reference. This patent describes the use of a nutritional supplement, *Spirulina platensis*, a blue green algae, grown in a highly enriched $^{13}CO_2$ environment. The $^{13}C$ incorporated into the algal biomass acts as a non-radioactive marker. A small amount of the labeled algae is baked into a roll or breakfast bar and consumed by a patient with juice or water. The meal is triturated by the stomach to a particle size of approximately 1-2 mm and then passes from the stomach through the pylorous into the intestine. In the intestine, the labeled products of $^{13}C$-Spirulina platensis digestion are absorbed and metabolized giving rise to labeled carbon dioxide expired in the breath. The rate of $^{13}CO_2$ appearance in the patient's breath ($^{13}CO_2$ excretion rate) is correlated to the rate of gastric emptying.

In contrast to scintigraphy, measurement of gastric emptying, in accordance with the marker described above, is indirect. Therefore, it is desirable to mathematically correlate the $^{13}CO_2$ excretion curve to the scintigraphic gastric retention curve so that the emptying time of the stomach can be calculated from the $^{13}CO_2$ curve. For example, one can use a general linear model to develop the relationship between diagnostic parameters obtained from scintigraphic measurements and the corresponding data obtained from the patient's $^{13}CO_2$ excretion rate when both the radioactive scintigraphic label and $^{13}C$ label are administered simultaneously in the same meal.

To accurately correlate the $^{13}CO_2$ excretion curve and the scintigraphic decay curve (which allows one to generate a predictive mathematical model from which a surrogate t1/2 gastric emptying rate may be calculated using only $^{13}CO_2$ excretion data), it is desirable to standardize the edible food and/or meal matrix delivering the marker to reduce the number of interfering variables. For example, if the new marker or drug (the surrogate marker) is incorporated into an edible food and/or meal (surrogate meal) that is different than the edible food and/or meal in which the well accepted marker or drug (predicate) is incorporated (predicate meal) the correlation process may be more difficult and or have poor predictive value. Thus, it is desirable for the predicate and surrogate meals to be as similar in composition, texture and nutritional content to each other as possible.

Similarly, such standardization allows for the validation of novel diagnostic or medical tests against well known, accepted tests ensuring accuracy and acceptance within the medical community. This may be particularly important where the new test detects, assesses, or measures physiological characteristics in a different manner, for example, indirectly versus directly.

In addition to standardization between novel and traditional medical tests, it is desirable that each individual method be standardized. It is also desirable that a medical test be performed identically each time it is conducted.

Thus, it is desirable to ensure reliability, reproducibility, accuracy and standardization when delivering a meal combined with a diagnostic marker or therapeutic drug into or beyond the stomach. It is further desirable to provide a reliable method of validating the performance of the novel (surrogate) marker and measuring the absorption and/or activity of the drug or marker.

Applicant has previously developed a lyophilized standardized gastric emptying test meal, as described in U.S. patent application Ser. No. 12/121,116. Applicant now desires to find alternative methods of producing standardized gastric emptying test meals which may also be used for gastric emptying tests.

SUMMARY OF THE INVENTION

Some embodiments provide a method of producing a standardized edible food labeled with a marker and the standardized edible labeled meal thus produced. In some embodiments, the method comprises the steps of: providing a marker, uniformly distributing a known amount of said marker throughout an edible food component, and, via the use of fluid bed processing, producing a final dry, storable, standardized meal with desirable marker, nutrient and caloric homogeneity. The marker can be incorporated through a biomass such as *Spirulina platensis*. The edible food component can comprise whole eggs, for example whole eggs that are derived from a liquid egg formulation specifically formulated for satisfactory taste, nutrient composition and caloric value.

In some embodiments, the method of producing a fluid bed standardized meal includes providing an edible food, providing a label, fluidizing the food and the label, and agglomerating the fluidized food and label to produce a final dry, storable, standardized meal with desirable marker, nutrient and caloric homogeneity. In other embodiments, the edible food can be the sole component that is fluidized in the fluid bed granulator chamber while the label can be put into solution or suspension and sprayed into the fluidized food powder to form the final particles. Alternatively, the label can be the sole component that is fluidized in the fluid bed granulator chamber while the food can be put into solution or suspension and sprayed into the label to form the final particles. Various arrangements suitable to the nature of the food and the label can be accommodated via the fluidized granulation process.

The method can further include drying the food and label, perhaps so that less than 3% moisture is present. The method can even further include packaging the dried food and label. The food can comprise, consist essentially of or consist of dry whole egg and the label can include dry labeled biomass, such as dry $^{13}C$ labeled *Spirulina platensis*. In some cases, the agglomeration includes applying atomized water to the fluidized food and label, perhaps at a rate of about 25 grams/minute. Of course, this rate can be adjusted during the agglomeration process.

The fluid bed standardized meals produced by these methods can have a binding capacity of at least about 100%, a relative standard deviation of less than about 6.0% (perhaps less than about 4.0%), a yield of final product of at least about 95% and/or an $a_w$ value of less than about 0.2. In some cases, the edible food includes food particles and the label includes label particles. The food particles can have a density that is different from (perhaps higher than) a density of the label particles. The food particles can also have a % moisture that is different from (perhaps less than) a % moisture of the label particles. For example, the food particles can have a moisture that is less than 3% and the label particles can have a % moisture that is less than 5%. Also, the food particles can have a particle size that is different from a particle size of the label particles. For example, the food particles can have a particle size of from about 355 to about 1,000 microns and the label particles can have a particle size of less than about 250 microns.

DETAILED DESCRIPTION OF THE PREFERRED EMBODIMENT

Applicant has discovered a fluid bed process that can be used to prepare a fluid bed standardized meal containing a known marker that is uniformly distributed throughout the food component. The fluid bed standardized meal can be used to measure physiological processes (in humans or other mammals) such as measurements of the rate of gastric emptying of a standardized meal, for assessment of absorptive and metabolic health and for diagnosing abnormalities and monitoring therapeutic interventions that may be associated with problems of gastrointestinal motility, absorption or metabolism of foods and substrates. The method includes providing a food in a dry form, such as a powdered or granulated form, providing a marker such as a $^{13}C$ labeled biomass or other chemical entity, and utilizing fluid bed processing methods to uniformly mix the food component with the marker. The result is a standardized gastric emptying test meal that is safe, efficient, diagnostically reliable, standardized and uniformly manufactured to regulatory standards suitable for oral pharmaceutical products and that can be readily used in a clinical setting. The terms fluid bed processing and fluid bed granulation are used interchangeably herein.

There are several advantages to using the described processes to prepare standardized meals. Fluid bed standardized meals provide a vehicle with reliably and accurately incorporated markers, such as a stable isotope labeled material or drug, into an edible food matrix. Fluid bed standardized meals also assure standardization of tests across all medical users and sites of administration. Various biological markers or drugs, and combinations thereof, can be incorporated and evaluated from the same meal matrix. Refrigeration is not required for fluid bed standardized meals, which makes them easier to store and prevents spoilage.

Fluid bed technology, utilized in embodiments of the invention, essentially fluidizes particles in an air environment inside a chamber. A fluidized bed is a bed of solid particles with a stream of air or gas passing upward through the particles at a rate great enough to set them in motion. As the air travels through the particle bed, it imparts unique properties to the bed. For example, the bed behaves as a liquid. Thus, the fluidized bed can be used to mix various powders or like materials to create a homogenous fluidized bed mixture, to dry wet product, agglomerate particles, improve flow properties of the particles to facilitate packaging, or produce coated particles and granules when moisture or other liquids are introduced to the process. Fluid bed granulation has never been used to combine both a food component and a diagnostic marker and/or other diagnostic or therapeutic materials into a standardized meal suitable for diagnosis and monitoring of disease and associated therapies in humans.

Applicant has discovered that fluid bed processing methods may be utilized to uniformly mix a food component with a marker such as $^{13}C$ labeled biomass, thereby producing particles, granules, pellets or other like entities of consistent food and $^{13}C$ homogeneity suitable for packaging, rehydrating, cooking and administration to the patient. The fluidization process allows the $^{13}C$ label to be integrated into and bind to the food so that the label does not separate from the food during digestion. When the meal is administered to the subject, the $^{13}C$ label remains integrated throughout the food and bound to the food. Hence, the $^{13}C$ label travels with the food reflecting the true rate of passage of the food that is undergoing digestion. If binding is not adequate, the label may separate from the food and enter the liquid phase during digestion, such that it is absorbed more quickly than the food, leading to inaccurate test results. However, embodiments of the invention avoid this problem by providing a meal in which the label is bound to the meal and remains bound during the digestion process to provide accurate test results.

Skilled artisans might expect that a gastric emptying meal prepared by the method of fluid bed granulation would not work. For example, in order for meals to be successful in diagnostic tests such as solid phase gastric emptying tests, the marker should remain bound to meal components during digestion. Skilled artisans would expect that the fluid bed granulation process could negatively affect the binding and digestive characteristics of both the meal and marker components. For example, in fluid bed granulation, both the food matrix particles and the marker particles are initially fluidized as dry particles. During the fluid bed granulation process, the particles are subjected to tremendous kinetic (mixing) forces, rehydration with atomized water (the amount of water used is approximately 50% by weight of the mass of the dried particles) and subsequently re-dried via warm filter air passing through the chambers. In addition, differences in both the nature, size and density of the food and marker particles could cause non or inconsistent coalescence of the marker particles to the food particles during fluid bed granulation processing. One would not know if the fluid bed granulation process would cause inconsistencies in the food component properties due to the food and marker matrices being subjected to the rugged fluid bed processing procedures. Important properties of the finished product could be affected. For example, the binding capacity of the marker to the food component could be affected if either the food or marker was mechanically or chemically changed during the process. However, Applicant has found that fluid bed granulation processing of previously dried foods, e.g. freeze-dried, milled formulated whole eggs, does not negatively affect the binding capacity of the marker to the food.

In certain embodiments, the edible food component can be any food in a dry powder or granulated form. For example, the food may be spray-dried or freeze-dried whole eggs that have been milled or otherwise broken up into a reasonably uniform powder or granulated form. The food may comprise whole eggs, for example whole eggs that are derived from a liquid egg formulation specifically formulated for satisfactory taste, nutrient composition and caloric value. Liquid whole eggs may be purchased commercially and subjected to a freeze-drying process in order to obtain dried eggs useful in embodiments of the invention.

The standardized meal into which the marker is to be incorporated may be any food type suitable for human consumption that may be acquired and/or made into a powdered, milled or granulated form. For example, typical meals used for gastric emptying tests have included scrambled eggs and liver. As will be appreciated by those skilled in the art, any food item that is amendable to a spray dry process, a freeze dry process or like process followed by appropriate milling may be utilized. Food items can be chosen to accommodate patients with special dietary needs, for example, vegetarians or those desiring food processed under Kosher standards.

In one embodiment, the standardized meal is eggs. Traditional scintigraphy methods have provided a meal consisting of a sandwich prepared with radio labeled grocery-bought eggs. Recent studies indicate that the $^{13}CO_2$ excretion curve derived from a biologically $^{13}C$ labeled meal correlates well with the gamma emission curve obtained from gastric scintigraphy. Further, specially formulated eggs are amendable to the spray dry process, freeze dry process or like process and have a long shelf life. Preferably, the eggs are whole eggs, which include both egg yolk and egg white.

The meal or edible food component of a meal can be labeled with a stable, biologically safe isotope, such as $^{13}C$. As will be appreciated by those skilled in the art, $^{13}C$ may be provided from any source that is suitable for human consumption. For example, octanoic acid incorporating $^{13}C$ may be mixed with the meal or edible food component of a meal. In one embodiment, the source of the $^{13}C$ is *Spirulina platensis*. This edible blue green algae containing $^{13}C$ may be obtained by growing the algal cells in a $^{13}C$ enriched environment as is disclosed in commonly assigned U.S. Pat. No. 6,872,516, the disclosure of which is herein incorporated by reference in its entirety. When consumed, the $^{13}C$ labeled compound, biomass or other chemical entity that, when consumed by the subject, will generate $^{13}C$ labeled carbon dioxide ($^{13}CO_2$) via digestion, absorption, metabolism or other physiological processes. The $^{13}C$ labeled carbon dioxide ($^{13}CO_2$) may be collected later by obtaining a sample of the breath of the subject.

As will be appreciated by those skilled in the art, the amount of algae or other source of $^{13}C$ to be added to the meal or component thereof will depend on a variety of factors including desired dosage, the amount of meal material, and the source of $^{13}$C. It is apparent that a plurality of meals can be produced according to the fluid bed granulation method. Once the marker is uniformly distributed in a meal or component thereof, individual servings can be produced by simply dividing the batch by weight, volume, or any other suitable technique.

The fluid bed standardized meal can be made with a variety of markers and applied to a wide array of meal types and can incorporate all types and amounts of markers, including those that are directly synthesized with $^{13}$C label or those derived through $^{13}$C labeling of biomasses like $^{13}$C-*Spirulina platensis*.

In one embodiment of the invention, a fluid bed standardized meal may be prepared using a freeze-dried, milled, specifically formulated whole eggs and dried powdered $^{13}$C labeled *Spirulina platensis* biomass in a ratio of 27 grams egg to 0.1 gram $^{13}$C—*Spirulina platensis* biomass. The egg and biomass may be introduced into fluid bed processing equipment such as a FL-M-1 Fluid Bed Production Unit manufactured by Freund Industrial Co., Ltd. (Tokyo, Japan). The egg and biomass may optionally be pre-mixed in a blender prior to introduction into the fluid bed equipment. Filtered air at 65° C. may be introduced to fluidize the components. Once fluidized, a carefully controlled atomized spray of water may be introduced to the process at a rate of 25 grams/minute. The egg particles and $^{13}$C—Spirulina platensis particles coalesce and with time (approximately 30 minutes or longer, depending on scale) and form homogenous particles composed of the blended materials. The atomized spray may be discontinued and the fluidized particles may be dried to less than 3% moisture, forming a blended powder/granulation of the two components. The resulting powder or granules, homogeneous in food matrix and $^{13}$C content, may then be unit dose packaged into smaller units and included as the primary test meal component of a diagnostic kit utilized for measurements of the rate of gastric emptying. The homogeneity and uniformity of each standardized egg meal ensures physiologic consistency and diagnostic reliability.

To ensure accuracy of test results, the $^{13}$C is desirably uniformly distributed throughout the edible meal or food component thereof. In one embodiment, the meal or component thereof and $^{13}$C labeled substrate (e.g. biomass substrate) are lyophilized separately. Subsequently, a pre-measured amount of lyophilized 13C substrate is thoroughly mixed with a pre-measured amount of specially formulated lyophilized egg as the primary ingredients to be introduced into the fluid bed processing chamber. The fluid bed processing method is employed yielding the fluid bed standardized meal. In this embodiment, no onsite preparation other than reconstitution and cooking, if necessary, is required to administer the fluid bed standardized meal.

In one embodiment, a large amount of liquid egg formulation is lyophilized or spray-dried to obtain a "master" batch of blank (unlabeled) dry egg suitable for use as the food component in the fluid bed granulation production process. Suitable liquid egg formulations can be obtained from USDA certified suppliers such as Willamette Farms, located in Newberg, Oreg. Preferably, the liquid egg formulations include whole eggs. After drying, the batch of blank egg can be milled to obtain relatively consistent particle size and can then be divided into sub-batches and stored. Later, one or more sub-batches of the master blank dried egg batch can then be retrieved for use in making a batch of fluid bed standardized meal. The marker that will be combined with the food component can be in a dry powder, suspension, crystalline or other dissolvable or dispersible form. In some cases, the marker includes a $^{13}$C labeled biomass such as $^{13}$C-*Spirulina platensis*. The marker can also be added to the food matrix in any desired amount. Finally, both the marker and the powdered blank egg component undergo the fluid bed granulation process together to provide a standardized, uniformly labeled meal that can be used in gastric emptying testing or measurements of other digestive or absorptive processes.

In other embodiments, the food element may be the sole dry component that is fluidized in the fluid bed granulator chamber while the marker may be put into solution or suspension and sprayed into the fluidized food powder to form the final particles. Alternatively, the marker may be the sole dry component that is fluidized in the fluid bed granulator chamber while the food element may be put into solution or suspension and sprayed into the chamber to form the final particles. Various arrangements suitable to the nature of the food and the marker utilized may be accommodated via the fluidized granulation process.

Applicant has found that creating master batches of an intended food component, e.g., whole powdered eggs, and master batches of a marker, e.g. $^{13}$C-*Spirulina platensis*, provide economic and regulatory benefits when utilizing fluid bed granulation technology. A large amount of an edible food component, for example, specifically formulated liquid whole eggs, can be produced or obtained at one particular point in time and then dried into a large batch. Thus, a single large batch of formulated egg, uniform in nutrient matrix and caloric value per the defined formulation, can be obtained and processed (dried and milled) at once, rather than repeatedly producing or obtaining food components just prior to the time a fluid bed granulation process is initiated. Utilizing small, independently produced batches of food and marker components for each standardized meal production is less economical due to redundancy in quality control procedures, quality control testing, labeling, packaging and stability testing overhead. However, certain embodiments allow for the utilization of small, independently produced batches. After producing the large master batch of food and/or marker material, the master batches can then be divided into any desired number of sub-batches and then stored. For example, a master food batch of 200 kilograms of dried egg may be produced by acquiring 741 kilograms of specifically formulated liquid egg (27% solids) which is then dried either by spray drying or lyophilization followed by milling. The batch is then protected in bulk, sealed packaging with low moisture and low $O_2$. Depending on the scale and equipment used in the fluid bed granulation process, multiple batches of fluid bed standardized meals may be made from this single lot of master food product, e.g., ten (10) 20-kilogram batches of fluid bed standardized meals may be made from a single 200-kilogram lot of the master food batch. Likewise, master batches of marker may also be made and likewise sub-divided for use in future fluid bed granulation batches.

At a desired time, one or more sub-batches of each component (food and marker) can be retrieved from the master lots and uniformly mixed via the fluid bed granulation process. The number of fluid bed standardized meal sub-batches that are produced from the master batches can be aligned closely with sales and inventory demand for diagnostic meals. In other words, when it is desired to make labeled, standardized meals, the stored sub-batches can easily be used, rather than having to produce or order fresh food components and/or fresh marker just prior to each batch. Hence, sub-lots of the master food and marker are then fluidized together to provide a batch of fluid bed standardized meal. This new batch of fluid bed standardized meal incorporating a marker can then be divided further into individual doses and unit-dose packaged to provide a standardized meal of consistent matrix, caloric value, marker content and marker uniformity to be inserted in a gastric emptying test kit intended to be administered to an individual patient. This production process allows for a manufacturer to consistently prepare highly standardized and uniform test meals incorporating a marker with more consistent materials, less burdensome quality control demands, and more closely aligned with sales and inventory demands.

An additional advantage of the fluid bed process is manufacturing speed. Master batches of food and marker materials take substantial time to prepare. Egg formulation, drying and packaging can take more than a month to produce a final meal product. Synthesis of markers and the related quality testing required to release the marker for use as an oral pharmaceutical has even longer lead times. However, because these materials can be made in large quantities in advance and kept available from master batches, the fluid bed granulation process employed to combine the materials and produce the finished fluid bed standardized meal powder can take less than 4 hours. Multiple batches can be prepared in a single day.

Percent binding recovery is a term used to describe the endpoint of a functional assay used to determine how much of a $^{13}C$ signal derived from a $^{13}C$ marker remains bound to the food component(s) of the standardized meal after in-vitro digestion utilizing U.S.P. (United States Pharmacopeia) gastric juice. In this assay, a meal with a marker is prepared in the same manner as that delivered to the patient. Half of the meal is assayed for $^{13}C$ content prior to digestion. The isotope ratio mass spectrometry signal specific to the $^{13}C$ content in the meal is determined. The second half of the meal then undergoes simulated in-vitro human gastric digestion. Remaining solids after simulated digestion are then recovered and analyzed for $^{13}C$ content. If the label is remaining bound to the solid components of the meal matrix, the signal observed from the digested meal should be substantially equal to or greater than that of the non-digested meal.

Applicant conducted a study to determine the percent binding recovery of a $^{13}C$ label in a specifically formulated $^{13}C$ labeled whole egg meal that has been has been prepared by the method of fluid bed granulation processing and compared the results to the percent binding recovery in a $^{13}C$ labeled meal of the same formulation that has been prepared using only lyophilization methods. The control meal had a binding capacity of 107.5%. As shown in Example 4, three test meal batches prepared by the method of fluid bed granulation, two using a FL-Multi I Flocoater fluid bed processor and one prepared by using a larger FLM-15 processor, both manufactured by Vector/Freund (Tokyo Japan), had binding capacities of 107.5%, 109.0% and 106.3% respectively. Thus, the test meal batches had a percent binding recovery that is substantially equal to the percent binding recovery of the control meal. Hence, the marker remains highly bound in a meal prepared by the method of fluid bed granulation.

The signal in the digested meal can be slightly higher than the pre-digested meal because the egg formulation utilized contains a small amount of skim milk solids. Although the skim milk solids contribute caloric value and taste, they are not involved in the binding of the label and are not retained in residual post-digested solids. Hence the concentration of $^{13}C$ is slightly higher in the remaining post-digested material compared to the pre-digested material originally containing the milk solids. On average, percent binding across multiple batches of fluid bed standardized meals prepared by the method of fluid bed granulation averages approximately 107.3%. Hence, the $^{13}C$ signal and binding attributes of meals prepared by the method of fluid bed granulation is excellent. Therefore, Applicant has discovered that the harsh kinetic forces, re-hydration and subsequent drying procedures involved in fluid bed granulation surprisingly does not hurt the binding and signaling capacity of $^{13}C$ and the digestive characteristics of the meal.

Another unpredictable element in the preparation of a standardized meal containing a marker by fluid bed granulation processing is the degree to which, if any, the marker particles would become integrated or coalesce with food matrix particles. Uniformity of marker throughout the food matrix is a desirable property in meals intended to measure gastric emptying, absorption or metabolic functions associated with a standardized meal. Uniformity results in diagnostic reliability. Furthermore, uniformity helps the ability of the product to meet the United States Food and Drug Administration's requirements (or those of other regulatory bodies) for dose uniformity in an oral pharmaceutical product. Sampling of the product across a completed batch of product intended for commercial distribution desirably demonstrates that the assay values of those samples have a dose uniformity relative standard deviation (RSD) of <6.0% to meet the Food and Drug Administration's cGMP requirements. A skilled artisan would not expect a low $^{13}C$ dose uniformity RSD in a fluid bed product due the differences in the food matrix and marker particle properties, e.g., density, moisture and size. In Applicant's development of fluid bed meals, dried egg particles (the food matrix) having a density of 0.4, <3% moisture and particle sizes ranging from 355 microns to 1,000 microns (averaging ~558 microns) were used. The dried marker particles ($^{13}C$-biomass) had a density of 0.33, <5% moisture and had been screened through a 250 micron screen so that all particles were <250 microns. Hence, uniform coalescence of the non-uniform particles unequal in density would not necessarily be expected. However, Applicant has found that indeed uniformity of the marker throughout the fluid bed granulated product is excellent. Two batches of fluid bed standardized meal produced by the method of fluid bed granulation using an FL-Multi 1 Flocoater resulted in excellent $^{13}C$ marker uniformity. Ten samples were obtained from each batch and analyzed in accordance with the USP Method 905 for content uniformity. The respective percent RSD's for each batch were 3.1% and 3.9%, which are almost 50% below the 6.0% limit. Likewise, three additional batches produced in the larger scale FLM-15 Flocoater demonstrated even tighter uniformity having RSD's of 3.0%, 2.5% and 1.4% respectively.

Of further concern was that the desired target concentration of marker in the fluid bed meal might not be achieved through fluid bed granulation. Previously described methods of preparing a standardized meal containing a marker, such as that described in Applicant's patent application Ser. No. 12/121, 116, Lyophilized Edible Food Incorporating a Marker and Methods of Making, filed May 15, 2008, are likely to hit the intended target concentration because during lyophilization of the formulated liquid egg containing the marker, only water is lost from the process through sublimation. The solids of the food matrix and the marker are not lost nor mechanically manipulated during the lyophilization process. In contrast, during fluid bed granulation processing, the materials are introduced into a chamber and fluidized via warmed air introduced at a rate of approximately 150-175 cfm (cubic feet per minute) or greater. To keep product from exiting the chamber but allowing the fluidizing air to escape during the production process, polyester cartridge filters are utilized as part of the granulator apparatus. Hence, one could not predict whether food matrix particles might escape or be preferentially bound to different components of the granulator apparatus thereby affecting the final concentration of the $^{13}C$ marker in the final product. Applicant found that by running the process under controlled conditions and pulsing the filters continuously throughout the granulation cycle, both the yield of final product (the weight of finished product at the end of the process compared to the sum of the weights of the beginning materials) and the $^{13}$C concentration target were surprisingly achievable. For example, Applicant produced a 500 gram batch of fluid bed standardized meal (using dried egg as the food component and dried $^{13}$C biomass as the marker component) utilizing the FL-Multi 1 Flocoater. During this process, 500 grams of dry milled egg was introduced into the granulator along with 1.8 grams of $^{13}$C labeled biomass. The biomass contained 42.6% $^{13}$C by weight. The total starting mass was therefore 501.8 grams. The mass of finished product recovered at the end of the process was 488.3 grams, or 97% of the starting weight. The concentration of the finished product (mg $^{13}$C/per gram of finished product) was 96% of the target concentration. Applicant can easily achieve a target of 100% by making a slight overage adjustment to the $^{13}$C marker being added to the batch. For example, Applicant repeated the same process for the same size batch in the same equipment utilizing a 3% excess of $^{13}$C labeled biomass. The yield for this batch was 99% and the product's concentration of $^{13}$C was 101% of the target concentration.

The batches described above were produced using a scale of approximately 33% of the capacity of the FL-Multi I Granulator. Applicant noted that the efficiency and yield of fluid bed granulators is optimized when the fluid bed system is operated at approximately 75-80% of its maximum capacity. In another example, Applicant scaled the process up using a FLM-15 Fluid Bed Flocoater (manufactured by Vector/Freund, Tokyo, Japan) to produce a batch size of 14.5 kilograms which represented 80% capacity of the FLM-15 Flocoater. The batch was manufactured by using 14,500 grams of the same formulated, dried egg used in the smaller Flocoater system and 52.2 grams of $^{13}$C biomass containing 41.56% $^{13}$C by weight. The yield was 100% and the concentration of $^{13}$C per gram of finished product was 99.6% of the target concentration. Three successive batches produced in the FLM-15 Flocoater had like yield and the $^{13}$C concentration averaged 100.3% of the target concentration.

Finally, because moisture is introduced to both the food and marker matrix during fluid bed granulation processing, it is desirable to dry the product to prevent spoilage. In some embodiments, the final product contains <3% moisture, especially for dry formulated egg mixes. Applicant's batches produced by fluid bed granulation can be consistently dried to less than <3% moisture (average=2.3%). The product may be conveniently dried within the fluid bed granulation machine, such as by continuous warm air flowing through the chamber.

To assess an associated property of dryness, those skilled in the art of food preservation utilize a property of a product known as water activity. Water activity, represented by the symbol, $a_w$, is a measure of the energy status of water in a food product. Low water activity is desirable, meaning the water is not readily available to microorganisms or processes that might participate in spoilage of the product. Various factors affect the degree to which water is "bound" in the product. These include colligative effects of dissolved solutes such as salt or sugar interacting with residual water through dipole-dipole, ionic, and hydrogen bonds, changes in hydrogen bonding between water molecules and surface interactions in which water may interact directly with chemical groups on ingredients such as starches and proteins through various chemical and hydrophopic bonds. Water activity instruments measure the amount of free (sometimes referred to as unbound or active water) in the product.

Achieving low water activity in Applicant's test meals is desirable for (1) optimizing the test meal for long shelf stability, (2) reducing the potential for degradation of ingredients in both the food matrix and the marker that are susceptible to chemical hydrolysis, (3) reducing the susceptibility of the test meals to microbial contamination and (4) reducing the burden and frequency of traditional microbial limits testing and screening for objectionable microorganisms.

Water activities required to support the growth of many microorganisms are well established. No objectionable organisms, including well-known pathogens such as *e. coli* and *staphylococcus aureus*, grow in an environment with water activity <0.6. Applicant's test meals, when prepared by the method of fluid bed granulation and dried to <3% moisture, demonstrate extremely low (superb) water activity levels. As described in Example 3, the $a_w$ values for three independent batches of Applicant's test meals incorporating a $^{13}$C labeled biomass marker were 0.16, 0.10 and 0.14, respectively. Three additional, successive batches produced in the FLM-15 Flocoater demonstrated $a_w$ values of 0.16, 0.16 and 0.10 respectively. Applicant's extremely low water activity assures product preservation, safety and excellent storability of the fluid bed meal.

It should be understood that the fluid bed standardized meal may be utilized to effectively and accurately incorporate and deliver any marker, isotope, or drug that is not susceptible to degradation during the fluid bed manufacturing process so that the marker or drug maintains its functional activity once the delivery meal is reconstituted. The method of fluid bed granulation used to prepare a standard meal wherein a marker or drug may be incorporated into one component of the meal may be used to deliver a marker or drug for use in any medical procedure where a physiological or diagnostic measurement is made following ingestion of a labeled edible food by the patient.

The fluid bed standardized meal may be used to assess gastric emptying in patients or test subjects. To utilize the meal, the clinical personnel can reconstitute, generally with a specific amount of potable water, the pre-labeled meal prior to the test. In some cases, the meal may be heated or cooked following reconstitution. For example, a 27 g pouch of $^{13}$C labeled powder utilizing formulated, dried whole egg may be re-hydrated with 4 ounces of water and cooked for 1.5 minutes in a microwave set at 1100 watts to form a uniformly labeled egg patty. The patient then ingests the meal, which includes the marker, for example, labeled algae. As the patient empties the meal to the small intestine, the $^{13}$C label, and the accompanying food components, is absorbed and metabolized resulting in the production of labeled carbon dioxide, specifically $^{13}CO_2$. The $^{13}CO_2$ is excreted in the breath of the patient. Breath samples are collected by techniques known in the art, at periodic time intervals, and the amount of $^{13}CO_2$ in the breath sample is determined by techniques known in the art.

For accurate results of solid phase gastric emptying measurements, the marker remains bound to the delivery vehicle, for example, an edible food component. If the marker becomes unbound it may move out in front of the solid phase emptying process into the liquid phase, passing through the pylorus and into the intestine faster than is representative of the actual solid phase gastric emptying process. Unbound marker may also pass through or be absorbed by the stomach wall and enter the circulation and metabolism process in a manner that gives rise to a $^{13}CO_2$ signal unrelated to the digestive process intended to be measured. Thus, the manufacturing process desirably does not change the nature of raw materials to the extent that binding capacity is lost.

In diagnostic tests using $^{13}$C, the amount of $^{13}$C administered is known. In a breath test, the results are based on the amount of $^{13}CO_2$ produced, which is directly related to the amount originally ingested. To determine the actual dosage of $^{13}$C, one looks at the weight percentage of total carbon, as well as the percent of $^{13}$C in the marker. This is shown in Table 1, which illustrates three different amounts of $^{13}$C label target dosages when utilizing the $^{13}$C-labeled algae species *S. platensis*. The amount of $^{13}$C labeled *S. platensis* that must be incorporated into a meal to achieve the target dose of $^{13}$C is determined according to the following equation:

Target dose mg $^{13}$C/($^{13}$C-Atom % X Total Carbon %)=mg [$^{13}$C]–*S. platensis* dispensed Table 1 provides several examples of how the equation is used. This calculation is applicable to $^{13}$C-labeled molecules or larger entities, such as a biomass.

Table 1. Example Calculation Of Dispensing To Achieve Three Target Dose Levels Of $^{13}$C.

TABLE 1

Example Calculation Of Dispensing To Achieve Three Target Doses Levels Of $^{13}$C.

| Target Dose Mg $^{13}$C | [$^{13}$C]-*S.p.* $^{13}$C-Atom % | [$^{13}$C]-*S.p* % Carbon | [$^{13}$C]-*S.p.* mg | Tolerance ±mg |
|---|---|---|---|---|
| 80 | 0.95 | 0.42 | 200 | 20 |
| 40 | | | 100 | 10 |
| 20 | | | 50 | 5 |

For *S. platensis*, the carbon content will generally be about 42%-44%, and the $^{13}$C incorporation about 95%, as shown in the table above.

In one embodiment where a meal is used for assessing gastric emptying, both a predicate $^{99m}$Tc label or meal and a surrogate marker or meal may be incorporated into the same meal matrix. In this case the $^{99m}$Tc label is added to the meal matrix at the site of administration due to its short radioactive-1/2 life-nature.

In one embodiment, the predicate meal is a fluid bed meal containing a $^{13}$C-surrogate marker. After the predicate meal is reconstituted, $^{99m}$Tc label is mixed into the meal just prior to cooking so that the radiolabel and $^{13}$C-surrogate marker become bound in the same specifically formulated food matrix. The patient then ingests the dual labeled meal and gastric emptying is measured simultaneously by the scintigraphy method previously described and the breath test method. The two measurements thus obtained are compared against each other and mathematically correlated. Since both the radiolabel and surrogate marker are incorporated into the same matrix, this embodiment allows for the reliable validation of a predicate meal type or predicate marker. By doing so, both tests are administered simultaneously eliminating the need to administer each test method independently on separate days. By putting both markers in the same specially formulated fluid bed meal and conducting each method concurrently, the effects of normal day to day biologic variation are eliminated, and, hence, correlation of the surrogate method to the predicate method can be assessed in the absence of normal day to day biologic variation exhibited in humans.

One advantage of establishing a fluid bed meal suitable for introduction of both a predicate and surrogate marker is that the meal may be used to test different dosages of labels to assure that there is sufficient label signal arising from the meal to make the appropriate physiologic or diagnostic conclusion. For example, prior to establishing a relationship between an established radioactive predicate label and a new non-radioactive $^{13}$C surrogate label, the appropriate dose of $^{13}$C to be incorporated in the meal via the method of fluid bed granulation to provide a reliable $^{13}CO_2$ excretion rate in the patient is determined. The signal is readily measurable, providing reliable data from which to establish the mathematical relationship between the predicate and surrogate marker.

The development of a surrogate meal that can be used to reliably validate the use of a surrogate marker or drug that is similar in texture, composition and nutritional value to a predicate meal and that may be readily incorporated into a commercially available meal/delivery system will allow for the substitution of stable non-radioactive labels for radioactive labels in test meals. Thus, in assessing physiological conditions such as gastric motility in women of childbearing age and in children where radiation exposure is undesirable, stable, non—radioactive markers may be used.

A multitude of assessments may be done using the fluid bed standardized meal containing gastric emptying markers described herein such as predicate and surrogate marker comparisons, measurement of intra-patient gastric motility variation, inter-patient rates of gastric emptying comparisons, establishment of normal ranges for gastric emptying in healthy individuals, establishment of cutoff points for differentiating normal from impaired subjects, establishment of critical limits of therapeutic efficacy, and the like.

Once validated against a well-characterized predicate method, e.g., gastric scintigraphy, a surrogate, non-radioactive labeled standardized fluid bed meal as described herein is well suited for diagnostic testing in the clinical setting. However, of particular importance is its use in heretofore difficult to perform large-scale epidemiological studies. Gastric scintigraphy is expensive, radioactive and requires specialized facilities and equipment. Aside from excessive cost, it cannot be used in epidemiological studies in children and women of childbearing age. Meals produced by the methods described herein are ideally suited to studies in which large populations may be simply, conveniently and safely tested to determine the prevalence of various gastric motility impairments. For example, the prevalence of gastroparesis as described in the medical literature varies highly because only a very limited number of small studies have been performed due to the limitations of gastric scintigraphy. Utilization of a $^{13}$C labeled standardized meals produced and validated in the way described herein may be conveniently and safely given to various populations suspected of gastroparesis in numbers sufficient to statistically validate the true prevalence of gastroparesis. Because the test is standardized, it may be given in a wide array of populations and locations. For example, it is thought that gastroparesis occurs primarily in diabetics, non-ulcer functional dyspepsia patients and in subsets of GERD (gastroesophageal reflux disease) patients. These populations may now be safely and conveniently tested in an outpatient epidemiological setting.

Ideally, the edible foods of the surrogate and/or predicate meals used in the clinical setting of the invention are prepared in a controlled food and/or pharmaceutical manufacturing environment meeting appropriate regulatory standards and have long term packaging stability with easy and reliable re-constitution techniques. In order to be used commercially for the diagnosis and monitoring of gastric emptying, absorption or metabolic disorders in humans, the gastric emptying meals with related markers are required by law to be produced in compliance with current good manufacturing practices applicable to pharmaceutical products since the product "will be used in the diagnosis or mitigation of disease." Production methods comply with the Food and Drug Administration's Quality System and Drug Manufacturing Regulations. These meals meet specific safety, uniformity, controlled manufacturing, stability, labeling and packaging requirements to be legally distributed and considered non-aldulterated product. Most importantly, the diagnostic consistency and reliability of the product is assured. One regulatory parameter is the uniformity of the dosage intended to be delivered to the patient. Appropriate sampling of the final dosage form of the meal meet a label uniformity standard of <6.0% relative standard deviation (% RSD).

Fluid bed manufacturing techniques facilitate the process of compliance with these regulations. The preparation of these fluid bed standardized meals in a manufacturing environment of this type ensures that the raw materials of the meals will not be randomly prepared at the site of test administration, which may lead to inaccuracies. For example, inconsistencies may arise from site to site due to differences in grocery type supplies, differences in cooking methods and times, and test administration techniques. Further, the use of a manufacturing process to prepare the edible food is beneficial because it allows not only for the production of a more "standardized" meal, but also for wide scale commercial use of the edible foods with an appropriate biological marker or drug consistent with regulatory requirements. For those meals that must be cooked at the testing site, it is best that the same method of cooking be applied to the predicate meal and the surrogate meal to minimize uncertainty. A fluid bed standardized meal can also serve as a standardized delivery mode for therapeutic drugs. Similarly an array of standardized meals prepared by the method of fluid bed granulation as described can be used to study the absorption of various diagnostic and/or therapeutic drugs with varying meal compositions. Further, a standardized meal prepared by the method of fluid bed granulation incorporating markers and/or therapeutic and diagnostic drugs can be used for animal studies in which food components, dosage of label or drug and amount of food by weight must be delivered with reliable control. In one embodiment, once a surrogate meal with its surrogate marker or drug has been established as useful by comparison to a predicate meal with the predicate marker or drug, using fluid bed technology to produce homogenous and uniform product ensures not only the stability and safety of the meal but the reproducibility of the test results obtained with such standardized meals.

Certain embodiments will be further described with reference to the following non-limiting Examples. It will be apparent to those skilled in the art that many changes can be made in the embodiments described in the Examples without departing from the scope of the present invention. Thus, the scope of the present invention should not be limited to embodiments described in this application, but only by the embodiments described by the language of the claims and the equivalents of those embodiments.

EXAMPLE 1

Preparation of $^{13}C$ Pre-Labeled Standardized Egg Meals

A liquid egg formulation was obtained from Willamette Farms, Inc., (Canby, Oreg.). The liquid egg was freeze-dried by Oregon Freeze Dry, Inc. (Albany, Oreg.) to produce a dried, milled, pasteurized, de-sugared whole egg formulated from whole eggs, water, nonfat dry milk, salt, and smoke flavoring. Dried, milled $^{13}C$ labeled *Spirulina* biomass containing 41.56% $^{13}C$ by weight (as determined by isotope ratio mass spectrometry) was provided by Advanced Breath Diagnostics, LLC (Brentwood, Tenn.). 14.5 kilograms (an amount equal to 80% of the FLM-15 Flocoater capacity) of the dried egg and 52.2 of the biomass were introduced to the processing chamber of an FLM-15 Fluid Bed Granulator. Fluidization was performed by VPS Corporation of Cranbury, N.J.

The number of meals derived from the process is calculated from the following formula:

$$14{,}500 \text{ grams dry egg powder}/27 \text{ grams per meal} = 537 \text{ unit dose meals}$$

The target $^{13}C$ concentration of the standardized meal is calculated as follows:

$$^{13}C\text{-}Spirulina \text{ charged to the system} := 52.2 \text{ grams}$$

$$\text{Total } ^{13}C \text{ contributed from } ^{13}C\text{-}Spirulina := (52.2) \times (41.56\%)$$
$$= 21.694 \text{ grams}$$
$$= 21{,}694 \text{ mg}$$
$$= 21{,}694 \text{ mg}/14{,}500 \text{ grams egg}$$
$$= 1.496 \text{ mg } ^{13}C/\text{gram of egg}$$

The egg and $^{13}C$-*Spirulina* powders were pre-mixed in a 2-cubic foot PK-V (shaped) blender for 5 minutes prior to insertion in the granulator chamber, a standard pre-blend process often utilized in fluid bed granulation technology. Clean, dry, pre-weighed polyester filters were installed in the granulator apparatus. After inserting the blended powders, the process was carried out utilizing filtered air at approximately 55° C. Air flow settings varying between 150 and 400 cfm were utilized to maintain fluidization of the powders and the emerging product throughout the process, including during the period in which atomized water is inserted into the process. After fluidization of the powders, atomized water was introduced to the system at rates varying between 50 and 125 grams/minute. During production, the filters were continuously pulsed every 30 seconds at 40 psi to avoid clogging the filters and/or retaining material on the filters. Once the process had run for a sufficient time to allow agglomeration that yields satisfactory uniformity of materials in the resulting granules, the coalescence of the particles was complete and the atomized water was discontinued. The fluidized product was dried to less than 3% moisture (as measured by Loss on Drying Mettler Method) by using continuous warm air flowing in the granulator apparatus. The entire granulation process took 105 minutes. Only 58 grams out of 14,552.2 grams of materials charged in the system was retained on the filters (<0.05%). After granulation and drying was complete, the fractional amount of material retained from the filters was combined with the bulk product retrieved from the granulator chamber and blended for 5 minutes, again utilizing a 2-cubic foot V blender.

The yield was 101.4% of the charged materials and the concentration (mg $^{13}C$/gram) was 98.1% of the expected (target) concentration. Also, the 14,500 grams of powdered egg charged to the system prior to processing contained 1% moisture. The finished product contained 2.2% moisture. Correcting for the weight contributed by the moisture difference, the process had a yield of 100% and the final product contained 99.63% of the target $^{13}C$ concentration. The water activity (at 2.2% moisture) was 0.14.

EXAMPLE 2

Confirmation of Uniform Distribution of Marker

Two 500 gram batches of fluid bed standardized meals were prepared using an FLM-1 Flocoater. The batches were prepared according to the method described in Example 1.

The two batches were tested for $^{13}C$ uniformity according to USP method 905: Content Uniformity. From each batch ten samples were randomly pulled from throughout the final bulk granulated powder. An aliquot of each sample was analyzed for $^{13}C$ content in a combustion chamber attached to an isotope ratio mass spectrophotometer and compared to a known $^{13}C$ standard.

The first batch contained 1.39 mg of $^{13}C$/gram of granulated powder. The standard deviation of the 10 samples was 0.04 and the percent relative standard deviation (% RSD) was 3.1%. The second batch contained 1.47 mg of $^{13}C$/gram of granulated egg. The standard deviation of across the ten samples was 0.06 and the % RSD was 3.9%. These results demonstrate that the $^{13}C$ label was uniformly distributed in the meal matrix. Uniformity of the $^{13}C$ label in fluid bed standardized meals is excellent and substantially tighter (by almost 50%) than the limit required for commercial pharmaceutical products.

EXAMPLE 3

Confirmation of Low Water Activity to Assure Product Stability and Safety

Water activity ($a_w$) is one attribute of a standardized meal prepared for use in diagnostic and therapeutic medicine. Low water activity is desirable for preservation of the product, shelf stability and as a defense against chemical or microbial spoilage of the product. To avoid microbial contamination and objectionable organism growth, the $a_w$ value must be <0.6.

The three batches of fluid bed standardized meals produced in Examples 1 and 2 were tested for water activity by utilizing a calibrated, commercially available Aqua Lab Water Activity Meter (Decagon Devices, Inc., Pullman, Wash.). Two of the batches were produced in a FL-Multi I granulator in Example 2 and 1 in an FLM-15 granulator in Example 1. All three batches were dried to <3% moisture. The respective $a_w$ values were 0.16, 0.10 and 0.14. Hence, these meals have $a_w$ values 4-fold below the 0.6 limit.

EXAMPLE 4

Evaluation of Binding Capacity

The three batches of fluid bed standardized meals produced in Examples 1 and 2 were also tested for binding capacity. A control lyophilized standard meal was also tested. For each meal, a granulated powder weighing 27 g and containing a known quantity of $^{13}C$ marker was reconstituted with 93 g of water, mixed, and cooked. The cooked meal was cooled, weighed and pressed through a 4 mm screen into a collection pan. An aliquot of the screened material, approximately 5 grams was collected, dried overnight at 100° C., and ground by mortar and pestle into a fine powder. Ten aliquots of the dried sample were combusted and assayed by gas isotope ratio mass spectrometry to determine the $^{13}C$ concentration.

The remaining portion of egg meal that remained in the pan after the screening procedure was divided into two equal amounts and subjected to in vitro digestion. U.S.P. gastric fluid was prepared by dissolving 2.0 g of NaCl, 3.2 g of purified pepsin derived from porcine stomach mucosa with an activity of 800-2500 units/mg protein and 7.0 mL of concentrated hydrochloric acid in 1 L of water.

The egg meal portions were incubated in 100 mL of the prepared gastric solution at 37° C. for 30 minutes with constant stirring at a fixed rate of 200±20 rpm using a stainless steel paddle apparatus located approximately 0.25 in from the bottom of the flask. After digestion, the contents of each flask were poured over a stacked set of 4 mm, 2 mm, and 1 mm screens and rinsed with cool tap water for 1 minute at a rate of approximately 4 L/min and the screening stack allowed to drain for 5 minutes. The weight of digested meal remaining on each screen was recorded and isolated in tarred aluminum sample pans. The samples were dried over night at 100° C. to remove excess water.

Five aliquots from each of the two post digested dried materials (ten in total) obtained from the 1 mm screen (the 1 mm size particles being representative of the smallest size a food particle reaches after the full triturating process) were analyzed for $^{13}C$ by combustion and isotope ratio mass spectrometry. The $^{13}C$ content of these samples was compared to the $^{13}C$ content of the pre (non) digested samples. The percent binding was calculated according to the following equation: ($^{13}C$ content per gram of Carbon post-digested meal)/($^{13}C$ content per gram of Carbon pre-digested meal)×100.

The mean value of the ten aliquots from the respective pre and post digested materials was calculated to determine the binding capacity of the sample. Their binding capacity values for the three meals were 107.5%, 109% and 106.3%. In comparison, the lyophilized control had a binding capacity of 107.4%. Hence, fluid bed granulation is a process that does not interfere with but rather confers excellent marker binding characteristics to the food matrix.

While preferred embodiments of the present invention have been described, it should be understood that various changes, adaptations and modifications may be made therein without departing from the spirit of the invention and the scope of the appended claims.

The invention claimed is:

1. A method of producing a fluid bed standardized meal comprising:
   providing an edible food to a fluid bed granulator chamber;
   providing a label to the chamber;
   fluidizing the food and/or the label, wherein fluidizing comprises passing a stream of air or gas through the food and/or label in the chamber;
   wherein, if either the food or the label is not fluidized, it is provided to the chamber as a solution or suspension; and
   after fluidizing the food and/or the label, agglomerating the food and label,
   wherein the food and label are not lyophilized after they are provided to the chamber, and
   wherein the fluid bed standardized meal is suitable for use in measuring gastric emptying in an individual.

2. The method of claim 1 further comprising drying the food and label.

3. The method of claim 2 further comprising drying the food and label so that less than 3% moisture is present.

4. The method of claim 2 further comprising packaging the dried food and label.

5. The method of claim 1 further comprising premixing the food and label.

6. The method of claim 1 wherein the food comprises dry whole egg.

7. The method of claim 1 wherein the label is a dry labeled biomass.

8. The method of claim 7 wherein the dry labeled biomass is dry $^{13}$C labeled *Spirulina platensis*.

9. The method of claim 1 wherein the agglomeration comprises applying atomized water to the fluidized food and label.

10. The method of claim 9 wherein the applying atomized water comprising applying atomized water at a rate of about 25 grams/minute.

11. The method of claim 1 wherein the fluid bed standardized meal has a binding capacity of at least about 100%.

12. The method of claim 1 wherein the fluid bed standardized meal has a $^{13}$C dose uniformity relative standard deviation of less than about 6.0%.

13. The method of claim 12 wherein the fluid bed standardized meal has a $^{13}$C dose uniformity relative standard deviation of less than about 4.0%.

14. The method of claim 1 wherein the edible food includes food particles and the label includes label particles, wherein the food particles have a density that is different from a density of the label particles.

15. The method of claim 14 wherein the food particles have a density that is higher than the density of the label particles.

16. The method of claim 1 wherein the edible food includes food particles and the label includes label particles, wherein the food particles have a % moisture that is different from a % moisture of the label particles.

17. The method of claim 16 wherein the food particles have a % moisture that is less than a % moisture of the label particles.

18. The method of claim 17 wherein the food particles have a % moisture that is less than 3% and the label particles have a % moisture that is less than 5%.

19. The method of claim 1 wherein the edible food includes food particles and the label includes label particles, wherein the food particles have a particle size that is different from a particle size of the label particles.

20. The method of claim 19 wherein the food particles have a particle size of from about 355 to about 1,000 microns and the label particles have a particle size of less than about 250 microns.

21. The method of claim 1 wherein the fluid bed standardized meal has a yield of final product of at least about 95%.

22. The method of claim 1 wherein the fluid bed standardized meal has a $a_w$ value of less than about 0.2.

23. The method of claim 1 further comprising establishing a target concentration and obtaining at least 95% of the target concentration.

* * * * *